(12) United States Patent
Zhang et al.

(10) Patent No.: US 9,775,762 B2
(45) Date of Patent: Oct. 3, 2017

(54) THREE-DIMENSIONAL SPINE CORRECTION ROBOT

(71) Applicant: Jilin Zhang, Beijing (CN)

(72) Inventors: Jilin Zhang, Jinan (CN); Yi Zhang, Jinan (CN)

(73) Assignee: Jilin Zhang, Jinan (CN)

(*) Notice: Subject to any disclaimer, the term of this patent is extended or adjusted under 35 U.S.C. 154(b) by 814 days.

(21) Appl. No.: 14/350,730

(22) PCT Filed: Oct. 9, 2012

(86) PCT No.: PCT/CN2012/082655
§ 371 (c)(1),
(2) Date: Apr. 9, 2014

(87) PCT Pub. No.: WO2013/053311
PCT Pub. Date: Apr. 18, 2013

(65) Prior Publication Data
US 2014/0309693 A1    Oct. 16, 2014

(30) Foreign Application Priority Data
Oct. 9, 2011    (CN) .......................... 2011 1 0300155

(51) Int. Cl.
*A61H 1/00*    (2006.01)
*A61H 1/02*    (2006.01)
*A61F 5/04*    (2006.01)

(52) U.S. Cl.
CPC .............. *A61H 1/008* (2013.01); *A61F 5/04* (2013.01); *A61H 1/00* (2013.01); *A61H 1/0218* (2013.01);
(Continued)

(58) Field of Classification Search
CPC .......... A61H 1/008; A61H 1/00; A61H 1/001; A61H 1/005; A61H 1/006; A61H 1/02;
(Continued)

(56) References Cited

U.S. PATENT DOCUMENTS

| 2005/0222524 A1* | 10/2005 | Fielding | A61H 23/04 601/98 |
| 2006/0048785 A1* | 3/2006 | Dalen | A61G 5/14 128/845 |
| 2008/0269030 A1* | 10/2008 | Hoffman | A61H 1/0218 482/142 |

FOREIGN PATENT DOCUMENTS

| CN | 1300581 A | 6/2001 |
| CN | 1539388 A | 10/2004 |

(Continued)

OTHER PUBLICATIONS

International Search Report issued in International Patent Application No. PCT/CN2012/082655 dated Jan. 3, 2013.

Primary Examiner — Justine Yu
Assistant Examiner — Colin W Stuart
(74) Attorney, Agent, or Firm — Oliff PLC

(57) ABSTRACT

A three-dimensional spine correction robot includes: a pillar, a seat, human body fixing belts, a head fixing apparatus, a bracket, pillar casing pipes, a spine lateral push-and-pull apparatus and a seat locking mechanism. The head fixing apparatus is fixed on the top of the bracket. The pillar casing pipes are movably sleeved over the pillar, and each pillar casing pipe is connected to a human body fixing belt. The lower end of the pillar casing pipe is connected to the seat, and the upper end is connected to the pillar. A first elastic connection object is connected between the pillar casing pipes. The spine lateral push-and-pull apparatus may move up and down along the pillar and swing. The seat is connected to the pillar through a bearing, and may move up (Continued)

and down along the pillar. The seat locking mechanism is fixed between the bracket and the seat.

16 Claims, 3 Drawing Sheets

(52) U.S. Cl.
CPC ......... *A61H 1/0229* (2013.01); *A61H 1/0292* (2013.01); *A61H 1/0296* (2013.01); *A61H 2001/0203* (2013.01); *A61H 2201/1207* (2013.01); *A61H 2201/1238* (2013.01); *A61H 2201/1284* (2013.01); *A61H 2201/1607* (2013.01); *A61H 2201/1621* (2013.01); *A61H 2201/1633* (2013.01); *A61H 2201/5064* (2013.01); *A61H 2203/0431* (2013.01)

(58) Field of Classification Search
CPC .. A61H 1/0218; A61H 1/0222; A61H 1/0229; A61H 1/0292; A61H 1/0296; A61H 2001/0203; A61H 2201/0149; A61H 2201/0138; A61H 2201/0119; A61H 2201/1284; A61H 2201/1253; A61H 2201/1604; A61H 2201/1607; A61H 2201/1609; A61H 2201/1611; A61H 2201/1619; A61H 2201/162; A61H 2201/1623; A61H 2201/1626; A61H 2201/1657; A61H 2201/1664; A61H 2203/0425; A61H 2203/0431; A61H 2203/0481; A61H 2205/02; A61H 2205/04; A61H 2205/08; A61H 2205/081
USPC ...... 606/237–245; 482/142, 143; 602/32–36, 602/38

See application file for complete search history.

(56) References Cited

FOREIGN PATENT DOCUMENTS

| CN | 2822564 Y | 10/2006 |
| CN | 101292936 A | 10/2008 |
| CN | 201631439 U | 11/2010 |
| JP | A-02-92353 | 4/1990 |

\* cited by examiner

THREE-DIMENSIONAL SPINE CORRECTION ROBOT

TECHNICAL FIELD

The present invention relates to the field of medical appliances and in particular to a three-dimensional spine correction robot used for treatment of spinal intervertebral diseases and for spine care.

BACKGROUND OF THE INVENTION

Spinal intervertebral soft tissue injury diseases, "intervertebral diseases" for short, including cervical spondylosis, prolapse of lumbar intervertebral disc, thoracic and lumbar posterior articular disorders and other spine-related diseases, are commonly and frequently encountered diseases, which have serious adverse effect on human health. Although the clinical manifestations of intervertebral diseases vary, the etiologies, pathologies and therapeutic principles thereof are basically the same. After many years of clinical research, the inventor believes the main cause of the diseases is adverse mechanical behaviors, like excessive spinal movement, overloading, etc., which result in the change (unbalance) of three-dimensional directions of intervertebral relative position and the injury of intervertebral soft tissue, especially the injury of the nerve roots and blood vessels from and to nerve root canals. Protrusion of intervertebral disc is just a manifestation of intervertebral soft tissue injury, instead of the main cause of the diseases. As the natural state is the optimal state, the preferred method for treatment of the diseases should be the most minimally invasive correction therapy, i.e., using a force without intervening in the human body to ensure the spinal intervertebral structure returns to or approaches the natural state. The surgical therapy is used only when the non-surgical therapy is ineffective.

As an indisputable fact, a plurality of doctors use the mechanical therapy, such as pulling, rotating, pushing, pressing and other hand techniques, to treat spinal intervertebral diseases including prolapse of lumbar intervertebral disc, etc., with obvious curative effect. Other than Chinese bone-setting massage techniques, US chiropractic techniques, European bone-setting techniques and the spine correction techniques of Japan, Thailand and Korea are also widely used and have obvious effect. The key steps thereof only include pulling, rotating, bending, extending, pressing, pushing, etc., which in essence belong to the mechanical therapy whereof the expression forms are pulling, pressing, bending, cutting and twisting. Most of the key therapies use the "sudden load", i.e., applying an appropriate sudden force for a patient without counteraction. With convenience and effectiveness as common features, the techniques often, quickly and effectively, heal the patients with mild diseases or getting the diseases for the first time.

However, the massage treatment and traction treatment also have many disadvantages, mainly including: 1) Impossible to be parameterized or quantified, various actions thereof belong to a mechanical therapy that is subject to the experience of therapists and is not accurate in terms of strength, wherein no curative effect is achieved if the strength or extent is too small and an injury may be caused if the strength or extent is too large; 2) As the intervertebral joint displacement or dislocation is three-dimensional directional, a therapist can only apply a unidirectional or bidirectional force each time in the massage of bone setting and is unable to apply a three-dimensional force on the lesion; 3) Although various traction devices are used in the traction treatment, all the devices carry out traction in a linear manner by controlling the traction force, instead of the distance, without sudden load, wherein the traction force is evenly distributed between the vertebrae and inaccurately positioned. Therefore, the effect of the massage and traction treatment is limited. In addition, the cycle of treatment course is too long and the curative effect for serious patients is not good.

SUMMARY OF THE INVENTION

In order to resolve the problems like poor effect, long cycle, etc. in the traditional massage and traction treatment for intervertebral diseases, the present invention provides a three-dimensional spine correction robot that may enhance the function of spine care and improve the comfort level and accuracy of the treatment. The three-dimensional spine correction robot comprises a pillar, a seat, a plurality of human body fixing belts, a head fixing apparatus, and a bracket, said head fixing apparatus is fixed on the top of the bracket, said three-dimensional spine correction robot further comprises a plurality of pillar casing pipes, a spine lateral push-and-pull apparatus and a seat locking mechanism; the pillar casing pipes are sleeved over the pillar in a movable manner, and each pillar casing pipe is connected to a human body fixing belt; the lower end of the pillar casing pipe is connected to the seat, and the upper end thereof is connected to the pillar; a first elastic connection object is connected between the pillar casing pipes; the spine lateral push-and-pull apparatus may move up and down along the pillar and swing; the seat is connected to the pillar through a bearing, and may move up and down along the pillar; and the seat locking mechanism is fixed between the bracket and the seat.

Said three-dimensional spine correction robot further comprises a lifting platform, the lifting platform is located below the seat and used to adjust the descent distance of the seat.

The lifting platform is connected to a displacement sensor for monitoring the descent distance of the seat.

Said three-dimensional spine correction robot further comprises an overall casing-pipe retractor device fixed between the upper end of the pillar casing pipe and the upper end of the pillar.

A second elastic connection object is connected between the human body fixing belts.

The head fixing apparatus comprises a helmet and a helmet rotation mechanism, the helmet rotation mechanism is fixed on the top of the bracket and connected to the helmet; the helmet is used to fix the head of a patient and to make quantitative rotation through the helmet rotation mechanism.

A weight or mechanical force is loaded around or below the seat.

A push rod is fixed and connected to one side of the seat to rotate the seat.

The spine lateral push-and-pull apparatus comprises a push-and-pull mechanism, a vertical positioning mechanism and a horizontal positioning mechanism; the vertical positioning mechanism may move up and down along the bracket and is fixed to the bracket; the push-and-pull mechanism comprises a push-and-pull rod and a driving mechanism for driving the push-and-pull rod, the bottom of the driving mechanism may be fixed in the sliding groove of the horizontal positioning mechanism in a movable manner.

Said three-dimensional spine correction robot further comprises a seat resetting mechanism so that the seat is capable of being returned to the initial position thereof.

Overcoming the disadvantages of treatment of cervical vertebrae, thoracic vertebrae and lumbar vertebrae respectively, the three-dimensional spine correction robot provided in the present invention is characterized by a scientific and reasonable structure, complete and accurate three-dimensional actions, high controllability, short treatment course, good curative effect, no damage to normal tissue, no iatrogenic injury, no pain, safety and reliability. The three-dimensional spine correction robot provided in the present invention may fix the dislocation between vertebrae, reduce the adhesion between the nerve roots and the surrounding tissue thereof, and ensure the intervertebral structure returns to or approaches the natural state. The three-dimensional spine correction robot provided in the present invention may not only be used for treatment of spinal intervertebral diseases, but also for spine care and healing degenerative spines.

DETAILED DESCRIPTION OF THE PREFERRED EMBODIMENT

The technical scheme of the present invention is further described below through the accompanying drawings and the preferred embodiment.

Figure 1:
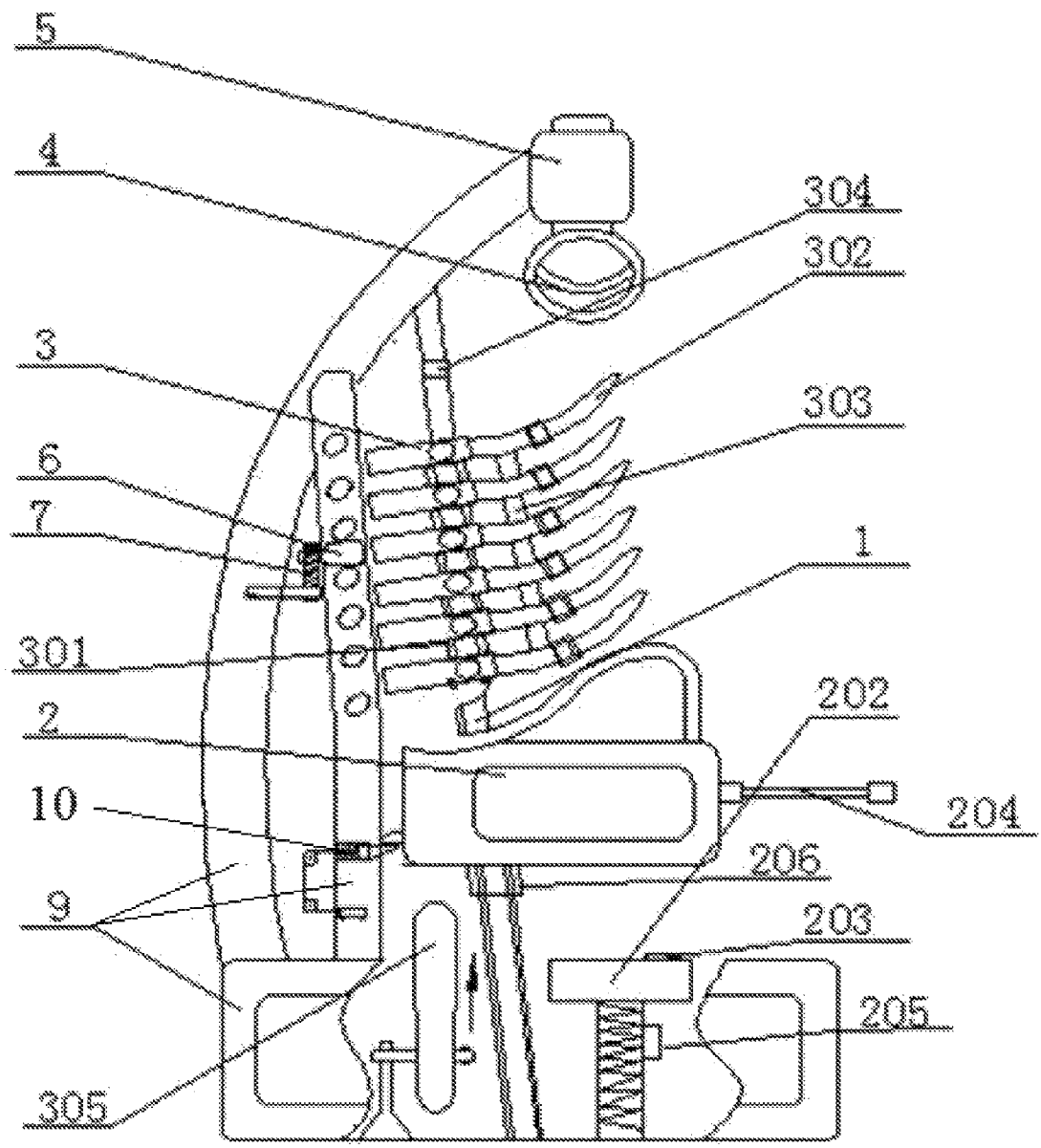
FIG. 1 is a side schematic structural view of the three-dimensional spine correction robot provided in the preferred embodiment of the present invention.
Figure 2:
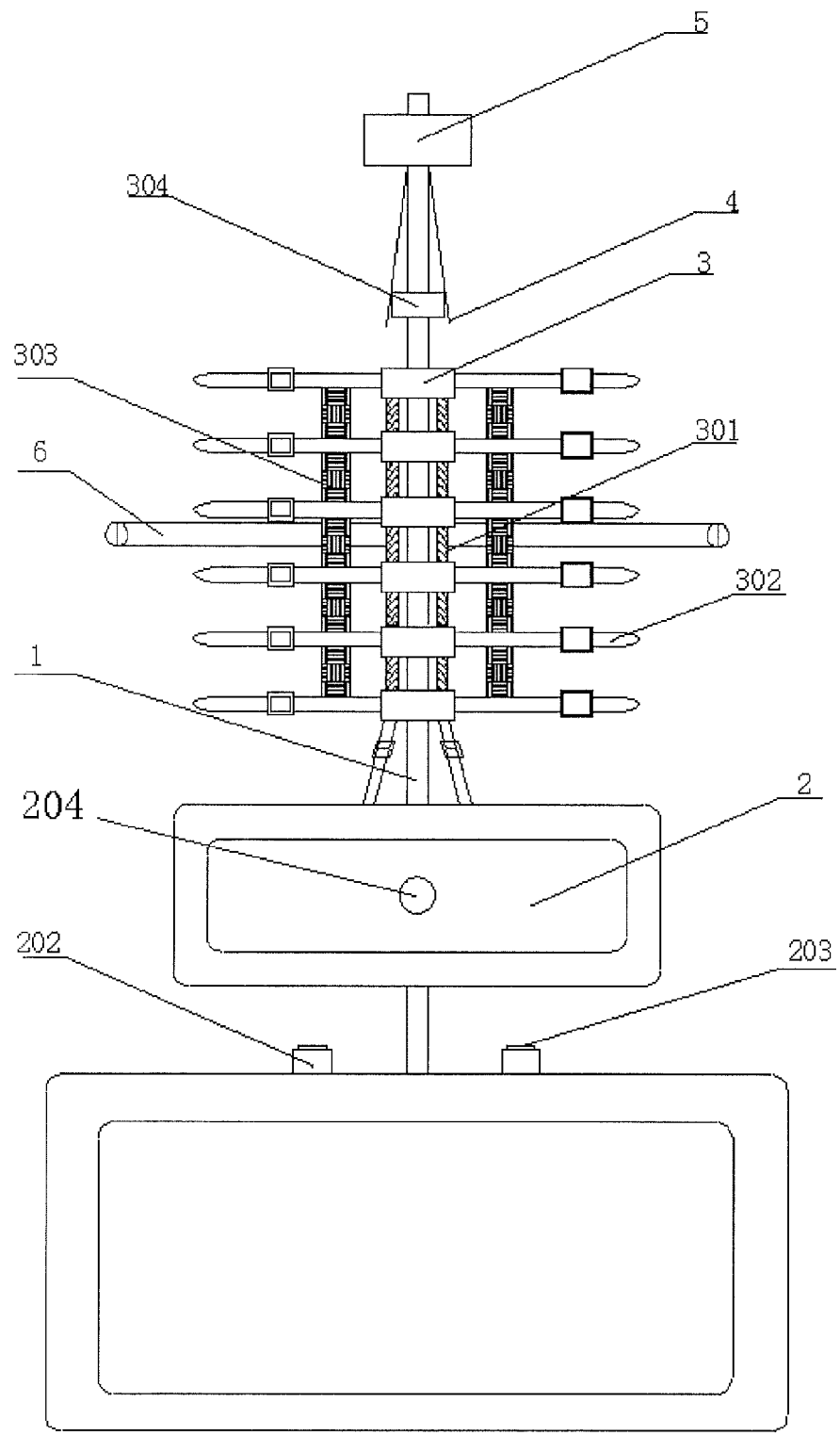
FIG. 2 is a front schematic structural view of the three-dimensional spine correction robot provided in the embodiment of the present invention.

Referring to FIG. 1 and FIG. 2, the preferred embodiment of the present invention provides a three-dimensional spine correction robot that may cure spinal intervertebral diseases, enhance the function of spine care and improve the comfort level and accuracy of the treatment. The three-dimensional spine correction robot comprises a pillar 1, a seat 2, a plurality of human body fixing belts 302, a head fixing apparatus, a bracket 9, a plurality of pillar casing pipes 3, a spine lateral push-and-pull apparatus 6, an overall casing-pipe retractor device 304 and a seat locking mechanism 10, wherein the head fixing apparatus is fixed on the top of the bracket 9; the pillar casing pipes 3 are sleeved over the pillar 1 in a movable manner, and each pillar casing pipe 3 is connected to a human body fixing belt 302; the lower end of each pillar casing pipe 3 is connected to the seat 2, and the upper end thereof is connected to the pillar 1; the pillar casing pipes 3 are interconnected by a first elastic connection object 301, such as steel spring, which may ensure the degenerative intervertebral discs of a patient align with the section, thus ensuring the force for spine correction is mainly applied to the lesion; the spine lateral push-and-pull apparatus 6 may move up and down along the pillar 1 and swing; the seat 2 is connected to the pillar 1 through a bearing 206, and may move up and down along the pillar 1; and the seat locking mechanism 10 is fixed between the bracket 9 and the seat 2.

The three-dimensional spine correction robot in the embodiment further comprises a lifting platform 202, the lifting platform 202 is located below the seat 2 and used to adjust the descent distance of the seat 2; the lifting platform 202 may also be connected to a displacement sensor 205 for monitoring the descent distance of the seat 2. In practical application, the lifting platform 202 is composed of a mechanical hoist and a steel plate.

The three-dimensional spine correction robot further comprises an overall casing-pipe retractor device 304 fixed between the upper end of the pillar casing pipe 3 and the upper end of the pillar 1.

In the embodiment, the human body fixing belts 302 are interconnected by a second elastic connection object 303, which may be woven with a plurality of rubber bands or strips.

In the embodiment, the head fixing apparatus comprises a helmet 4 and a helmet rotation mechanism 5, the helmet rotation mechanism 5 is fixed on the top of the bracket 9 and connected to the helmet 4; the helmet 4 is used to fix the head of a patient and to make quantitative rotation through the helmet rotation mechanism 5; the helmet rotation mechanism 5 may be powered by a torque motor or an actuating motor.

The three-dimensional spine correction robot further comprises a seat resetting mechanism 305 so that the seat 2 is capable of being returned to the initial position thereof. In the embodiment, the seat resetting mechanism 305 is a cam mechanism. When the seat 2 descends and touches the trigger switch 203 thereof, which is located on the lifting platform 202, the cam starts to rotate to lift the seat 2 gradually; when the top of the cam mechanism reaches the highest point, the seat 2 returns to the initial locking position. In addition, the seat resetting mechanism 305 may also be implemented with an electromagnetic mechanism or another mechanism. The seat resetting mechanism may be implemented other than as specifically described in the preferred embodiment of the invention, provided that the seat 2 may return to the initial locking position thereof.

Figure 3:
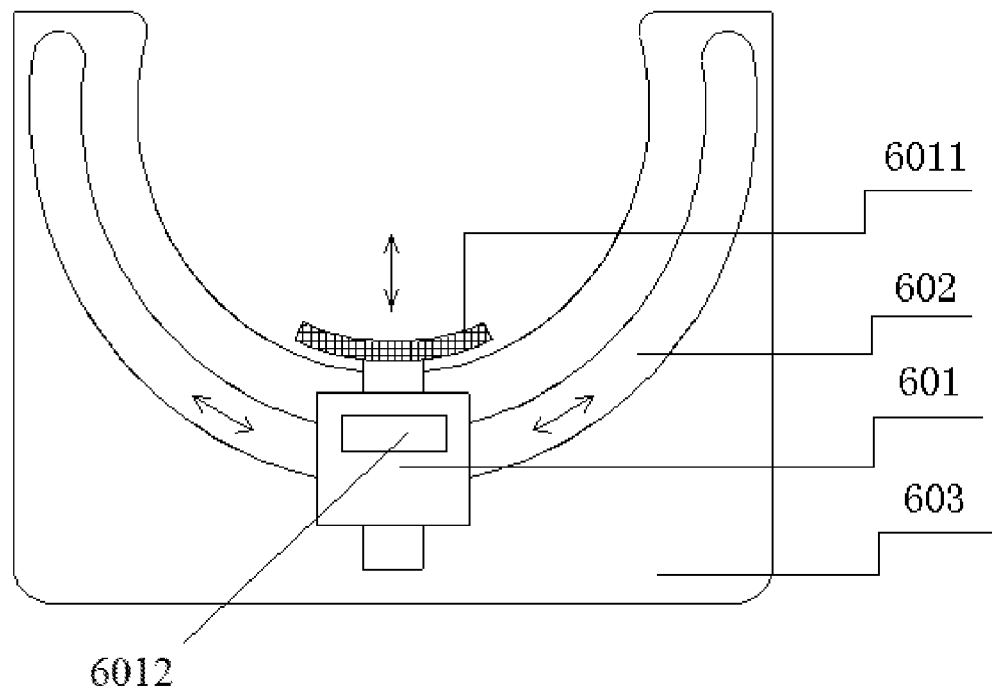
FIG. 3 is a top view of the spine lateral push-and-pull apparatus in the embodiment of the present invention.

Referring to FIGS. 1 and 3, the spine lateral push-and-pull apparatus 6 comprises a push-and-pull mechanism 601, a vertical positioning mechanism 7 and a horizontal positioning mechanism 603. The vertical positioning mechanism may move up and down along the bracket 9 and is fixed to the bracket 9. The push-and-pull mechanism 601 comprises a push-and-pull rod 6011 and a driving mechanism 6012 for driving the push-and-pull rod 6011, the bottom of the driving mechanism may be disposed in the sliding groove 602 of the horizontal positioning mechanism 603 in a movable manner and fixed to a certain position in the sliding groove 602, which corresponds to the location of degenerative vertebrae. Driven by the driving mechanism, the push-and-pull rod may move forwards and backwards to cause a spine to move forwards, backwards, leftwards or rightwards or rotate by changing the point of strength, thus making quantitative displacement of certain vertebrae in order to ensure the intervertebral structure approaches the natural state. The driving mechanism may be implemented by a motor machine or a hydraulic machine.

Figure 4:
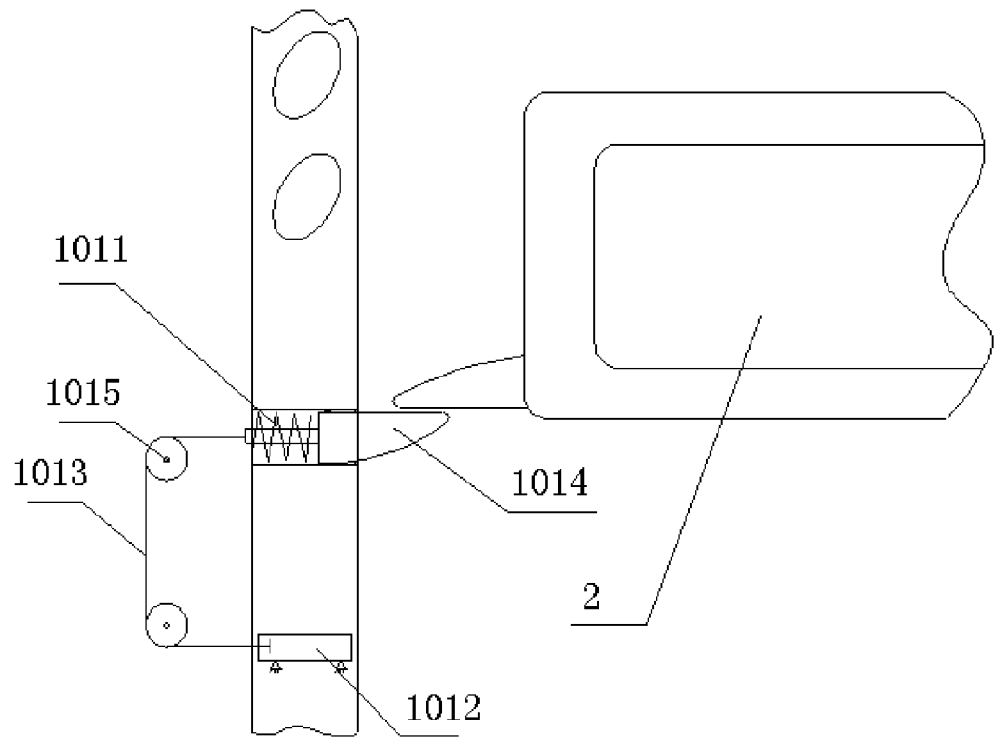
FIG. 4 is a schematic structural view of the seat locking mechanism in the embodiment of the present invention.

Referring to FIG. 4, the seat locking mechanism 10 comprises a telescopic torsion spring 1011, a toggle button 1012, a steel wire 1013, a pin 1014 and two fixed pulleys 1015, wherein the telescopic torsion spring 1011 is sleeved over the connecting rod of the pin 1014; one end of the steel wire 1013 is connected to the connecting rod of the pin 1014, and the other end thereof is connected to the toggle button 1012 through the two fixed pulleys 1015. When the treatment begins, the toggle button 1012 is flipped to pull the pin 1014 inwards via the steel wire 1013, so that the telescopic torsion spring 1011 is pressed tightly and the pin 1014 is separated from the plug welded on the seat 2, thus the seat 2 falls freely; when the toggle button 1012 is released, the telescopic torsion spring 1011 is reset to push the pin 1014 outwards; when the seat 2 is lifted up by the seat resetting mechanism 305, the plug welded on the seat 2 impacts the pin 1014 to cause the pin to retract inwards immediately, so that the plug moves across the pin 1014 to cause the seat 2 to return to the initial position thereof.

In practical application, the instantaneous falling speed of the seat 2 may be increased by putting a weight around the seat 2 or fixing an external driving device between the seat 2 and the lifting platform 202. In addition, at one side of the seat 2, e.g., at the left, right or front side thereof, a push rod 204 is connected in a fixed manner to rotate the seat 2. In the embodiment, the push rod 204 is fixed and connected to the front side of the seat 2, which may be rotated in the range from 0 degree to 50 degrees according to the requirements for treatment or enhancement.

In practical application, each pillar casing pipe 3 has a central hole and is sleeved over the pillar 1 through the hole. The horizontal two ends of each pillar casing pipe 3 bend forwards to form an arch-like shape, and the far end thereof is connected to a human body fixing belt 302. Each pillar casing pipe 3 may be connected to a human body fixing belt 302 in a plurality of ways, such as button connection, riveted connection, stitched connection, etc.

In spine correction or the treatment of thoracic and lumbar intervertebral diseases, a patient should sit on the seat 2. The overall casing-pipe retractor device 304 is used to adjust the interval between the pillar casing pipes 3 according to the height of the patient, and the human body fixing belts 302 are used to fix the chest and waist respectively. According to the height, weight, pathological degree, pathological position and other conditions of the patient, the distance between the seat 2 and the point of fall and the rotation direction and angle of the seat 2 are set and adjusted to meet the requirements for treatment. Furthermore, the spine lateral push-and-pull apparatus 6 is positioned to be level with the degenerative vertebrae, and the acting point and scalability thereof are confirmed. After examination and confirmation, the action execution mechanisms may be started up to ensure the falling and rotation of the seat 2, the lateral pushing and pulling of the spine are carried out in a coordinated and synchronized manner, thus fixing the dislocation between vertebrae, correcting the locations of vertebrae and reducing the adhesion between the intervertebral soft tissue in particular, the nerve roots and the surrounding tissue thereof to ensure the intervertebral structure approaches the natural state.

In the treatment of cervical spondylosis, a patient should sit on the seat 2. The human body fixing belts 302 are used to fix the chest and waist respectively. According to the height, weight, pathological degree, pathological position and other conditions of the patient, the distance between the seat 2 and the point of fall is set and adjusted. Fixed by the helmet 4, the head is positioned according to the requirements for treatment; furthermore, the rotation direction and angle of the helmet rotation mechanism 5 are determined to meet the requirements for treatment. After examination and confirmation, the action execution mechanisms may be started up to ensure the falling of the seat, the rotation of the helmet and other actions are carried out in a coordinated and synchronized manner, thus achieving the purpose of treatment of cervical spondylosis or correction of a degenerative spine.

Compared to the prior art, the three-dimensional spine correction robot in the embodiment of the present invention has the following advantages:

1. Overcoming the disadvantages of treatment of cervical vertebrae, thoracic vertebrae and lumbar vertebrae respectively, the three-dimensional spine correction robot is characterized by a scientific and reasonable structure, complete and accurate three-dimensional actions, high controllability, and high operability after integration with computer programs.

2. As the distance of fast falling is subject to the height of the seat, the three-dimensional spine correction robot improves the safety and reliability while reducing noises.

3. Characterized by short treatment course, good curative effect, no damage to normal tissue, no iatrogenic injury and no pain, the three-dimensional spine correction robot may fix the dislocation between vertebrae, reduce the adhesion between the nerve roots and the surrounding tissue thereof and ensure the intervertebral structure returns to or approaches the natural state.

4. The three-dimensional spine correction robot in the present invention may not only be used for treatment of spinal intervertebral diseases, but also for spine care and healing degenerative spines.

The preferred embodiment further describes the objects, technical scheme and beneficial effects of the present invention in detail. It should be understood that the foregoing description is only intended to illustrate a specific embodiment of the invention and not to limit the invention. Any modification, equivalent replacement and improvement made to the embodiment without departing from the spirit and principles of the invention should fall within the protection scope of the invention.

The invention claimed is:

1. A three-dimensional spine correction robot comprises a pillar, a seat, a plurality of human body fixing belts, a head fixing apparatus, and a bracket, said head fixing apparatus is fixed on a top of the bracket, wherein said three-dimensional spine correction robot further comprises a plurality of pillar casing pipes, a spine lateral push-and-pull apparatus and a seat locking mechanism; the plurality of pillar casing pipes are sleeved over the pillar in a movable manner, and each of the plurality of pillar casing pipes is connected to a respective one of the plurality of human body fixing belts; a lower end of the plurality of pillar casing pipes is connected to the seat, and an upper end of the plurality of pillar casing pipes is connected to the pillar; a first elastic connection object is connected between the plurality of pillar casing pipes; the spine lateral push-and-pull apparatus is adapted to move up and down along the pillar and swing; the seat is connected to the pillar through a bearing, and is adapted to move up and down along the pillar; and the seat locking mechanism is fixed between the bracket and the seat.

2. The three-dimensional spine correction robot of claim 1, wherein said three-dimensional spine correction robot further comprises a lifting platform, the lifting platform is located below the seat and used to adjust a descent distance of the seat.

3. The three-dimensional spine correction robot of claim 2, wherein the lifting platform is connected to a displacement sensor for monitoring the descent distance of the seat.

4. The three-dimensional spine correction robot of claim 3, wherein said three-dimensional spine correction robot further comprises an overall casing-pipe retractor device fixed between the upper end of the plurality of pillar casing pipes and an upper end of the pillar.

5. The three-dimensional spine correction robot of claim 4, wherein a second elastic connection object is connected between the plurality of human body fixing belts.

6. The three-dimensional spine correction robot of claim 4, wherein the head fixing apparatus comprises a helmet and a helmet rotation mechanism, the helmet rotation mechanism is fixed on the top of the bracket and connected to the helmet; the helmet is used to fix the head of a patient and to make quantitative rotation through the helmet rotation mechanism.

7. The three-dimensional spine correction robot of claim 4, wherein a weight or mechanical force is loaded around or below the seat.

8. The three-dimensional spine correction robot of claim 4, wherein a push rod is fixed and connected to one side of the seat to rotate the seat.

9. The three-dimensional spine correction robot of claim 4, wherein the spine lateral push-and-pull apparatus comprises a push-and-pull mechanism, a vertical positioning mechanism and a horizontal positioning mechanism; the vertical positioning mechanism is adapted to move up and down along the bracket and is fixed to the bracket; the push-and-pull mechanism comprises a push-and-pull rod and a driving mechanism for driving the push-and-pull rod, a bottom of the driving mechanism is adapted to be fixed in a sliding groove of the horizontal positioning mechanism in a movable manner.

10. The three-dimensional spine correction robot of claim 4, wherein said three-dimensional spine correction robot further comprises a seat resetting mechanism so that the seat is capable of being returned to an initial position thereof.

11. The three-dimensional spine correction robot of claim 1, wherein a second elastic connection object is connected between the plurality of human body fixing belts.

12. The three-dimensional spine correction robot of claim 1, wherein the head fixing apparatus comprises a helmet and a helmet rotation mechanism, the helmet rotation mechanism is fixed on the top of the bracket and connected to the helmet; the helmet is used to fix the head of a patient and to make quantitative rotation through the helmet rotation mechanism.

13. The three-dimensional spine correction robot of claim 1, wherein a weight or mechanical force is loaded around or below the seat.

14. The three-dimensional spine correction robot of claim 1, wherein a push rod is fixed and connected to one side of the seat to rotate the seat.

15. The three-dimensional spine correction robot of claim 1, wherein the spine lateral push-and-pull apparatus comprises a push-and-pull mechanism, a vertical positioning mechanism and a horizontal positioning mechanism; the vertical positioning mechanism is adapted to move up and down along the bracket and is fixed to the bracket; the push-and-pull mechanism comprises a push-and-pull rod and a driving mechanism for driving the push-and-pull rod, a bottom of the driving mechanism is adapted to be fixed in a sliding groove of the horizontal positioning mechanism in a movable manner.

16. The three-dimensional spine correction robot of claim 1, wherein said three-dimensional spine correction robot further comprises a seat resetting mechanism so that the seat is capable of being returned to an initial position thereof.

* * * * *